(12) United States Patent
Allen

(10) Patent No.: US 9,168,086 B2
(45) Date of Patent: *Oct. 27, 2015

(54) REMOVABLE INK FOR SURGICAL INSTRUMENT

(71) Applicant: COVIDIEN LP, Mansfield, MA (US)

(72) Inventor: Charles D. Allen, Broomfield, CO (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/456,751

(22) Filed: Aug. 11, 2014

(65) Prior Publication Data

US 2014/0350544 A1 Nov. 27, 2014

Related U.S. Application Data

(60) Continuation of application No. 14/028,231, filed on Sep. 19, 2013, now Pat. No. 8,821,490, which is a division of application No. 12/632,017, filed on Dec. 7, 2009, now Pat. No. 8,540,709.

(51) Int. Cl.
*A61B 18/18* (2006.01)
*A61B 18/14* (2006.01)
*A61B 19/00* (2006.01)
*A61B 18/12* (2006.01)
(Continued)

(52) U.S. Cl.
CPC .................. *A61B 18/14* (2013.01); *A61B 18/12* (2013.01); *A61B 19/44* (2013.01); *A61B 19/46* (2013.01); *A61B 18/1445* (2013.01); *A61B 18/1477* (2013.01); *A61B 18/1815* (2013.01); *A61B 18/20* (2013.01); *A61B 2018/0097* (2013.01); *A61B 2018/00178* (2013.01); *A61B 2018/1425* (2013.01); *A61B 2019/442* (2013.01); *A61B 2019/4815* (2013.01); *A61M 2205/273* (2013.01); *A61M 2205/6072* (2013.01)

(58) Field of Classification Search
CPC .......................... A61B 19/44; A61B 2019/442
USPC .................................... 606/1, 32, 41; 600/198
See application file for complete search history.

(56) References Cited

U.S. PATENT DOCUMENTS 5,374,813 A 12/1994 Shipp
5,411,295 A * 5/1995 Bates et al. ..................... 283/81
(Continued)

FOREIGN PATENT DOCUMENTS

EP 2113219 A2 11/2009
WO 9633242 A2 10/1996

OTHER PUBLICATIONS

European Search Report for European Application No. 10193962 dated Apr. 12, 2011.

*Primary Examiner* — Joseph Stoklosa
*Assistant Examiner* — Jocelyn D Ram

(57) ABSTRACT

The present disclosure relates to an apparatus and method for preventing reuse of a surgical instrument. The single-use surgical instrument includes a housing, an electrical connector and a treatment component. Indicia may be printed on the housing, the electrical connector and/or the treatment component. A removable ink is applied to any portion of the surgical instrument in the form of indicia that is readable by a scanning device. The removable ink includes a protein-based composition that is reactivateable with a sterilization solution having an enzyme-based composition such that upon sterilization, the removable ink reacts with the sterilizing solution and becomes unreadable by the scanning device.

7 Claims, 3 Drawing Sheets

(51) Int. Cl.
    *A61B 18/20*     (2006.01)
    *A61B 18/00*     (2006.01)

(56)           References Cited

U.S. PATENT DOCUMENTS

| | | | |
|---|---|---|---|
| 5,489,531 A   |         | 2/1996  | Benson |
| 5,569,163 A * | 10/1996 | Francis et al. ............... 600/133 |
| 5,810,944 A   | 9/1998  | Smitkowski et al. |
| 5,895,075 A * | 4/1999  | Edwards ......................... 283/81 |
| 6,117,685 A * | 9/2000  | Omatsu et al. ................ 436/135 |
| 6,238,623 B1* | 5/2001  | Amhof et al. ................. 422/426 |
| 6,485,978 B1* | 11/2002 | Kirckof et al. ..................... 436/1 |
| 6,485,979 B1* | 11/2002 | Kippenhan et al. ................ 436/1 |
| 6,488,890 B1* | 12/2002 | Kirckof ......................... 422/403 |
| 6,489,276 B1  | 12/2002 | Gibbs |
| 6,648,223 B2  | 11/2003 | Boukhny et al. |
| 6,651,669 B1  | 11/2003 | Burnside |
| 6,659,036 B2* | 12/2003 | Omatsu et al. ................ 116/206 |
| 6,753,306 B2   | 6/2004  | Simpson |
| 6,776,341 B1   | 8/2004  | Sullivan et al. |
| 6,847,490 B1*  | 1/2005  | Nordstrom et al. ........... 359/642 |
| 6,884,394 B1*  | 4/2005  | Hehenberger et al. ........ 422/404 |
| 7,268,684 B2   | 9/2007  | Tethrake et al. |
| 7,362,228 B2   | 4/2008  | Nycz et al. |
| 8,540,709 B2   | 9/2013  | Allen |
| 8,821,490 B2   | 9/2014  | Allen |
| 2002/0188259 A1* | 12/2002 | Hickle et al. .................. 604/189 |
| 2005/0239349 A9  | 10/2005 | Desinger |
| 2005/0261551 A1* | 11/2005 | Couvillon ..................... 600/118 |
| 2006/0069305 A1* | 3/2006  | Couvillon et al. ............. 600/117 |
| 2006/0236913 A1  | 10/2006 | Wills |
| 2006/0244652 A1  | 11/2006 | Tethrake et al. |
| 2007/0219563 A1* | 9/2007  | Voegele ......................... 606/108 |
| 2008/0255607 A1* | 10/2008 | Zemlok ......................... 606/205 |
| 2009/0065565 A1  | 3/2009  | Cao |
| 2009/0266289 A1* | 10/2009 | Greene et al. ................. 116/206 |
| 2010/0076266 A1* | 3/2010  | Boulais et al. ................ 600/142 |

* cited by examiner

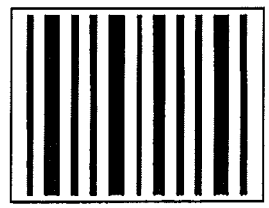
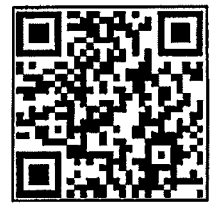
FIG. 2A          FIG. 2B
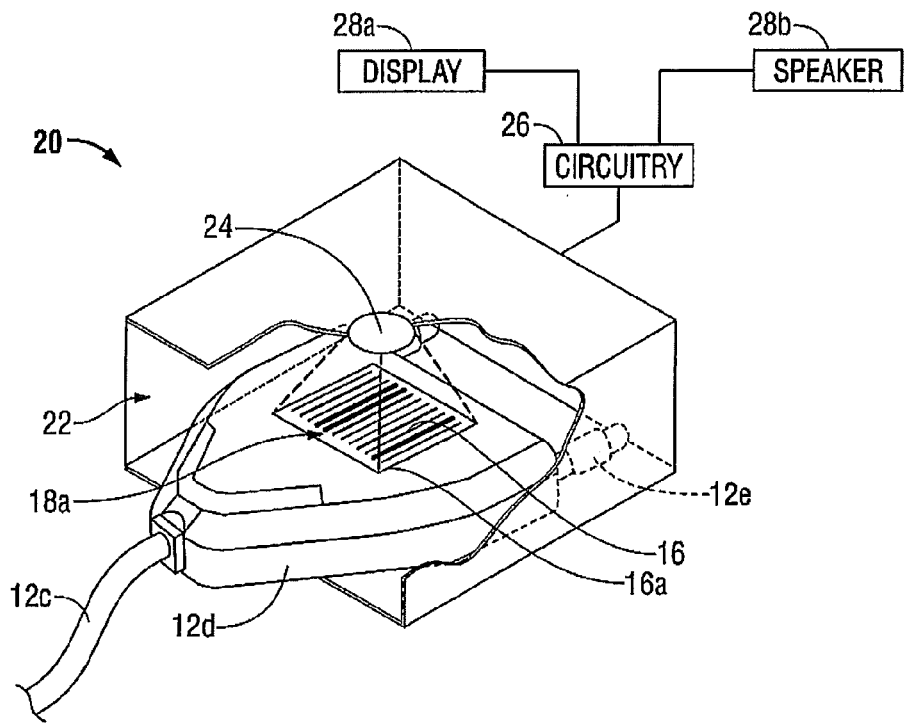
FIG. 3

REMOVABLE INK FOR SURGICAL INSTRUMENT

CROSS REFERENCE TO RELATED APPLICATIONS

This application is continuation of U.S. application Ser. No. 14/028,231, filed Sep. 16, 2013, which is a divisional of U.S. application Ser. No. 12/632,017, filed Dec. 7, 2009, the entire contents of which are incorporated herein by reference.

BACKGROUND

1. Technical Field

The present disclosure relates to electrosurgical instruments, systems and methods and more particularly, the present disclosure relates to electrosurgical instruments, systems and methods that include a removable ink configured to substantially prevent re-use of an electrosurgical instrument after a surgical procedure.

2. Description of Related Art

During a surgical procedure, it is common for an operator to use one or more surgical instruments throughout the surgical procedure. Some of the various surgical instruments may include re-usable instruments and/or disposable instruments. After a completed or partial surgical procedure, the single-use surgical instruments are disposed of in proper waste compartments, while the multi-use surgical instruments are cleaned and sterilized by common cleaning procedures known in the art.

Typically, a common cleaning procedure includes an initial "pre-soak" step and a final sterilization step. In the "pre-soak" step, the multi-use instrument is soaked in common cleaning agents that are commonly found in hospitals and clinics. These common cleaning agents usually contain enzyme solutions that are necessary to dissolve blood from blood-soiled surgical instruments. Afterwards, in the sterilization step, the instruments are sterilized by an autoclave system, gamma sterilization, and/or ethylene oxide (ETO) system that prepares the instruments for use in a later surgical procedure.

In certain situations, the single-use surgical instruments are, mistakenly or negligibly, sterilized in the same manner as multi-use instruments and then re-used in another surgical procedure. However, due to certain manufacturing designs and other limitations, single-use instruments are not intended to be sterilized and re-used, since re-using may create a potential risk due to certain parts being made from unsterilizable and/or unautoclavable components or cross infection caused by microbiological contamination between surgical procedures.

SUMMARY

The present disclosure provides for a method for preventing reuse of a surgical instrument. The method includes an initial step of providing a surgical instrument that includes a portion configured to accept indicia printed thereon. In another step, a removable ink is applied to the portion of the surgical instrument in the form of indicia. The removable ink includes a protein-based composition reactivateable with a sterilization solution that has an enzyme-based composition. In another step, the surgical instrument is validated for an initial use by reading the removable ink applied to the surgical instrument.

The method may further include the steps of using the instrument for a surgical procedure and using the sterilizing solution such that the sterilizing solution reacts with the removable ink to at least partially dissolve the removable ink rendering the removable ink unreadable. The step of validating may include using a scanning device to read the removable ink applied to the surgical instrument.

The present disclosure also relates to a single-use surgical instrument that includes a housing, an electrical connector and a treatment component. Indicia may be printed on the housing, the electrical connector and/or the treatment component. A removable ink is applied to any portion of the surgical instrument in the form of indicia that is readable by a scanning device. For example, the removable ink may also be applied to a connector, a shaft, a housing, an end effector, a handle, an actuator, a rotation mechanism, an articulation mechanism and/or a switch. The removable ink includes a protein-based composition that is reactivateable with a sterilization solution having an enzyme-based composition such that upon sterilization, the removable ink reacts with the sterilizing solution and becomes unreadable by the scanning device.

In embodiments, the scanning device may be, for example, an optical scanner, an electrical scanner or a magnetic scanner. The scanning device may be adapted to couple to an electrosurgical energy source. The removable ink may be configured in the form of a one-dimensional code, a two-dimensional code or a three-dimensional code.

BRIEF DESCRIPTION OF THE DRAWINGS

Various embodiments of the subject instrument are described herein with reference to the drawings wherein:

FIG. 2A is a top view of a one-dimensional bar code, in accordance with an embodiment of the present disclosure;

FIG. 2B is a top view of a two-dimensional bar code, in accordance with an embodiment of the present disclosure;

FIG. 3 is a perspective view of a connector plug of the electrosurgical system of FIG. 1 having a removable ink in a first configuration and disposed within the receptacle of the electrosurgical energy source;

DETAILED DESCRIPTION

Figure 1:
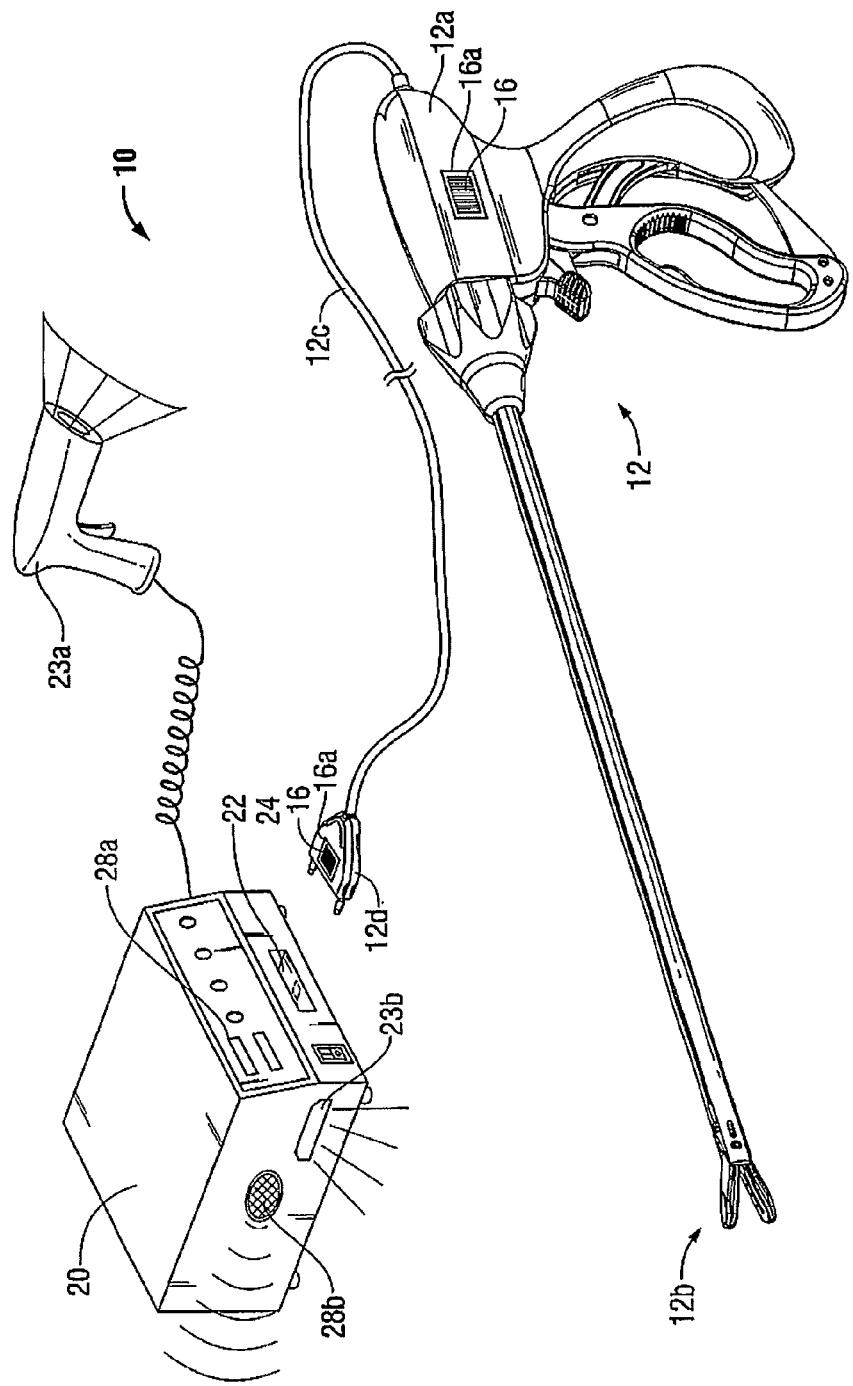
FIG. 1 is perspective view of an electrosurgical system that includes an electrosurgical energy source and an electrosurgical instrument, in accordance with an embodiment of the present disclosure.

Embodiments of the presently-disclosed electrosurgical instrument are described in detail with reference to the drawings wherein like reference numerals identify similar or identical elements. As used herein, the term "distal" refers to that portion that is further from an operator while the term "proximal" refers to that portion that is closer to an operator. In addition, the phrase "single-use instrument" refers to a surgical instrument that is designed and configured to be used in only one surgical procedure. Also, the term "re-use" refers to when an operator uses a surgical instrument for a second time, after a first surgical use. It is important to note that a single surgical procedure may include using multiple single-use instruments of the same kind.

In general, the present disclosure relates to a surgical instrument including a removable or dissolvable ink having a first configuration that logically communicates with an electrosurgical energy source (e.g., a generator 20) and a dissolved or second configuration that becomes unreadable, electrically, optically, or magnetically. The removable ink may take the form of any suitable identifying indicia that is read by various components of the electrosurgical source. After an electrosurgical operation has been performed and the instrument has been thoroughly sterilized, the removable ink is completely or substantially dissolved or removed thus rending the ink unreadable. In other words, in this dissolved configuration the electrical, optical or magnetic reader is unable to read the identifying indicia, thus preventing logical communication to the electrosurgical instrument regarding validation of the surgical instrument or other operatory parameters. The novel system, apparatuses, and methods of the present disclosure are discussed in greater detail below.

Referring now initially to FIG. 1, an embodiment of the presently disclosed electrosurgical system is shown generally as 10. The system 10 includes an electrosurgical instrument 12 (e.g., endoscopic forceps) that is logically coupled to generator 20. The electrosurgical instrument 12 includes an end effector assembly 12b configured to treat a patient and a housing 12a that stores the various internal operating components of the electrosurgical instrument 12.

End effector assembly 12b may be, for example, but not limited to, a jaw assembly, a pencil-style electrode assembly, or any other suitable type of electrosurgical electrode assembly. Additionally, end effector assembly 12b may be configured to provide any suitable type of electrosurgical energy, for example, but not limited to radiofrequency energy and microwave energy.

A connector plug 12d is operably coupled to the housing 12a and connects instrument 12 to generator 20 via a flexible insulated wire or cable 12c. Cable 12c is disposed between connector plug 12d and electrosurgical instrument 12 and carries electrosurgical energy (e.g., high frequency energy) from one or more mechanical attachments to electrosurgical instrument 12. Cable 12c allows variable movement of electrosurgical instrument 12 relative to generator 20.

Electrosurgical system 10 further includes an area of removable ink 16 disposed on electrosurgical instrument 12. At least a portion of the electrosurgical instrument 12 is configured to accept the removable ink 16 and/or label 16a (which will be discussed below) in the form of indicia (e.g., two-dimensional bar code and three-dimensional bar code). Removable ink 16 may be disposed directly on any portion of electrosurgical instrument 12, for example, but not limited to connector plug 12d or housing 12a. Other areas of the instrument 12 are also contemplated, for example, handle, actuator, articulation mechanism, end effector, rotary assembly, etc. Additionally or alternatively, removable ink 16 may be disposed on any applicable substrate, for example, a flexible label material 16a. In this manner, label 16a may be directly applied or affixed to electrosurgical instrument 12 and removable ink 16 may be applied directly on label 16a. One skilled in the art may find applying removable ink 16 directly onto electrosurgical instrument 12 easier and more economical than applying removable ink 16 onto label 16a and then applying label 16a to instrument 12, or vice versa.

In one embodiment, removable ink 16 is a protein-based ink that dissolves, bleeds or otherwise reacts with enzyme-based or sterilizing cleaning solutions. Other types of inks (i.e., non protein-based) may be used to make up removable ink 16 and may still serve the same purpose of dissolving when placed in contact with sterilizing solutions, e.g., enzyme-containing cleaning solutions or the like. Other types of removable inks 16 may include, but not be limited to, protein-based materials including gelatin, collagen, hard or soft keratin, and other materials including waxes, polymeric materials (e.g., water-based), sugar-based substrates or water-soluble plastics such as polyvinyl alcohol (PVOH) and environmentally-safe chemicals or so called "green" chemicals (e.g., vegetable-based).

Application of the removable ink 16 to an electrosurgical instrument 12 may vary. As mentioned above, removable ink 16 may be applied directly onto electrosurgical instrument 12 or on a label 16a. In one example embodiment, removable ink 16 may be printed on a roll of labels 16a, such that, the roll of labels 16a may be easily shipped and later applied onto various types of instruments. In another embodiment, removable ink 16 may be directly printed onto electrosurgical instrument 12 by a printing device. More specifically, removable ink 16 may be printed by an ink jet printer or by an ink pad printing process. The ink pad printing process initially requires a pre-formatted roller stamp to roll over an ink pad containing removable ink 16. Subsequently, the roller stamp rolls over a pre-determined portion of electrosurgical instrument 12 and leaves a pre-formatted print of removable ink 16 on instrument 12.

In one embodiment, removable ink 16 may take the configuration of a bar code. FIGS. 2A and 2B illustrates some of the various types of bar code configurations that may be utilized by system 10. For example, removable ink 16 may be a one-dimensional bar code 18a (shown in FIG. 2A) or a two-dimensional bar code or Aztec code 18b (shown in FIG. 2B). A three-dimensional or hologram bar code may also be utilized. In this manner, when bar code 18a, 18b is positioned on the instrument 12 (e.g., on connector plug 12d), a sensor 24 disposed within or associated with generator 20 is able to identify and validate the surgical instrument 12 and activate the generator 20 for surgical treatment or configure the generator 20 based on the type of instrument connected thereto. The interactions between generator 20 and connector plug 12d, via removable ink 16, will be discussed in greater detail further below.

In another embodiment, removable ink 16 may take the form of a logo or any other suitable indicia that may be placed on any suitable portion of electrosurgical instrument 12. In other example embodiments, a removable liner may be disposed atop removable ink 16 for protection of removable ink 16 during shipping and/or storage. Prior to use, the removable liner may be removed by an operator prior to validation of the instrument 12.

As discussed above, removable ink 16 may be either directly disposed on electrosurgical instrument 12 or disposed on label 16a, which, in turn, is positioned on electrosurgical instrument 12. In the particular embodiments shown with reference to FIGS. 3 and 4, removable ink 16 is formed as a bar code 18a, 18b disposed on label 16a attached to connector plug 12d. Generator 20 is able to read the bar code 18a, 18b via any suitable sensor(s), for example, electrical, optical and/or magnetic.

In another embodiment, a scanner or reader may be a hand held scanner 23a that is operably connected to generator 20. Hand held scanner 23a allows an operator to readily and easily scan bar code 18a, 18b prior to activating electrosurgical instrument 12. Additionally or alternatively, a scanner or reader 23b may be mounted, fixed or otherwise conveniently disposed on the generator 20 or a component attached to the generator 20.

Figure 4:
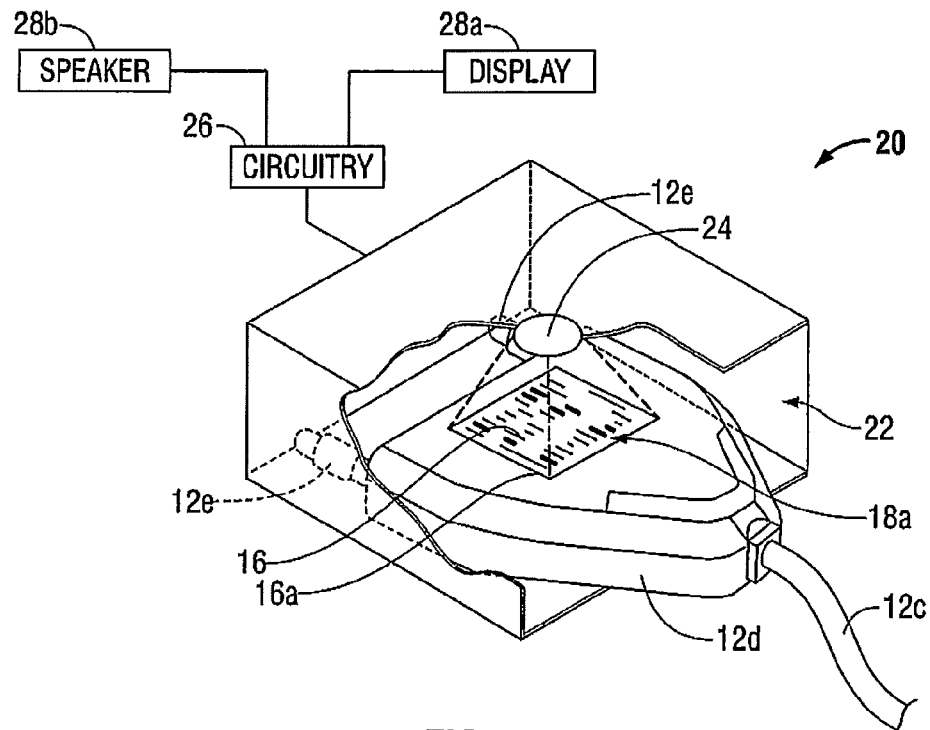
FIG. 4 is a perspective view of the connector plug of the electrosurgical system of FIG. 1 having the removable ink in a second configuration and disposed within the receptacle of the electrosurgical energy source.

As best shown in the figures, connector plug 12d is disposed between the electrosurgical instrument 12 and generator 20. Generator 20 is configured to transmit treatment energy through connector plug 12d to the electrosurgical instrument 12 and to a patient via end effector assembly 12b. The connector plug 12d may also be configured to communicate logical information from the electrosurgical instrument 12 to the generator 20, as shown in FIGS. 3 and 4, by virtue of the bar code 18a, 18b and/or Aztec code or some other indicia imprinted thereon. An instrument identifying circuit (e.g., electrical, optical, magnetic, etc.) may be used to facilitate recognition and identification of the type of electrosurgical instrument 12 connected to generator 20 and verification that the instrument is configured for initial use (i.e., calibration of the various parameters in the generator 20) and has not been previously used in a prior surgery.

As mentioned above, connector plug 12d includes prongs 12e that mechanically attach within receptacle 22 of generator 20, for example, by a male/female fitting arrangement. Prongs 12e may be made of any suitable conductive material, for example, but not limited to gold, copper, and stainless steel. Essentially, prongs 12e create an electrical connection between electrosurgical instrument 12 and generator 20 for delivery of high frequency energy. As mentioned above, generator 20 includes receptacle 22 that is configured to receive connector plug 12d. Receptacle 22 may also be utilized to contain any suitable sensor for indentifying and/or recognizing the presence of connector plug 12d is positioned therewithin and for communicating logical information to and from the instrument and verify the integrity of the instrument prior to use.

The generator 20 may be, for example, a source of high frequency energy, but may also be a laser, hydro dissector, aspirator or other medical or surgical delivery system. In an embodiment of the present disclosure, generator 20 includes a control panel 20a for providing a graphical user interface for an operator. Generator 20 may further include a display 28a and a speaker 28b that are configured to provide visual and/or audible information regarding the status of the connection between energy source 20 and electrosurgical instrument 12. For example, a visual and/or audible indication is provided to the operator if instrument 12 is not connected properly to generator 20 or the instrument integrity is suspect (i.e., an instrument has been previously used and sterilized).

As shown in FIGS. 3 and 4 and by way of example, an optical sensor 24 is positioned within receptacle 22 and is configured to read bar code 18a, 18b, when connector plug 12d is inserted into receptacle 22. More specifically, removable ink 16 is readable when the instrument 12 is used for the first time. Receptacle 22, via optical sensor 24, may also be configured to detect the type of connector plug 12d that is inserted therein and logically communicate electrical information via any suitable circuitry to generator 20. To accomplish this purpose, generator 20 may include an instrument identifying circuitry 26 that provides various pre-set surgical parameters between generator 20 and electrosurgical instrument 12 that relate to treating tissue with the particular electrosurgical instrument 12. Bar code 18a, 18b may also include programmable data that is read by optical sensor 24 of receptacle 22 and programs the generator 20 to specific electrical parameters prior to surgical use.

The bar code 18a, 18b may be relatively simple logic (e.g., "on" and "off") or complex logic (e.g., programming instructions, instrument data, etc.) depending upon a particular purpose. In other words, the bar code 18a, 18b may be simply employed as a verification to confirm the integrity of the instrument 12 or contain additional information relating to the configuration of the instrument 12. As mentioned above, during manufacturing and assembly, the bar code 18a, 18b is encoded and placed on the instrument 12 or instrument connector plug 12d. The operator simply places the instrument 12 into the instrument reader (e.g., optical sensor 24) or scans the instrument 12 (e.g., laser scanner 23a, 23b) to verify the integrity of the instrument prior to use. Once verified through simple logic or identification circuitry, the generator 20 may be activated to begin surgical treatment. Label 16a (and bar code 18a, 18b) may be constructed such that the label 16a is not easily removed from the instrument 12 to prevent tampering or the adhesive utilized with the label 16a may be dissolvable with a protein-based enzyme (or other type of sterilization enzyme mentioned above) such that the label 16a peels off or otherwise detaches from the instrument 12 during sterilization.

In addition, the removable ink 16 is dissolvable when the ink 16 is submersed (or otherwise comes in contact with) a protein-based enzyme (or other type of sterilization enzyme mentioned above) such that during a typical sterilization process, the removable ink 16 dissolves, smears or otherwise become unreadable. It is important to note that the removable ink 16 and/or the label 16a adhesive are not dissolvable when in contact with water, saline solution, blood or other liquids commonly associated with a surgical environment. As such, during surgery, the integrity of the label 16a and the "readability" of the removable ink 16 remain intact enabling continued use of the instrument 12 for a single surgical procedure. Only during sterilization, is the integrity of the label 16a and/or removable ink 16 compromised.

Referring now to FIG. 4, an example embodiment of connector plug 12d is shown having a dissolved or partially removed bar code 18a, 18b after having been subjected to a sterilization post surgery. More specifically, removable ink 16 is unreadable by conventional readers (e.g., optical, electrical and magnetic). For example, optical sensor 24 and/or laser scanner 23a, 23b will not recognize the presence of instrument 12 (i.e., plugged into receptacle) since sensor 24 and/or laser scanner 23a, 23b is unable to read the removable ink 16 or label 16a in the second configuration. In this manner, the sensor circuitry communicates to display 28a and/or speaker 28b an error message. The error message may be an audible and/or a visual message that communicates to an operator that instrument 12 is plugged in, however, energy will not be communicated to the instrument 12.

Additionally or alternatively, the error message may communicate to an operator and/or generator 20 that no instrument is being detected. Any suitable error message may be displayed as long as the operator is notified that instrument is compromised. In other words, if the single-use instrument has been sterilized or cleaned with a sterilizing solution after a surgical operation, then suitable circuitry and/or sensors of generator 20 will not read the bar code to validate the integrity of the instrument 12 or will recognize and communicate to the operator and/or generator 20 that instrument 12 has been used and/or is not operable.

Figure 5:
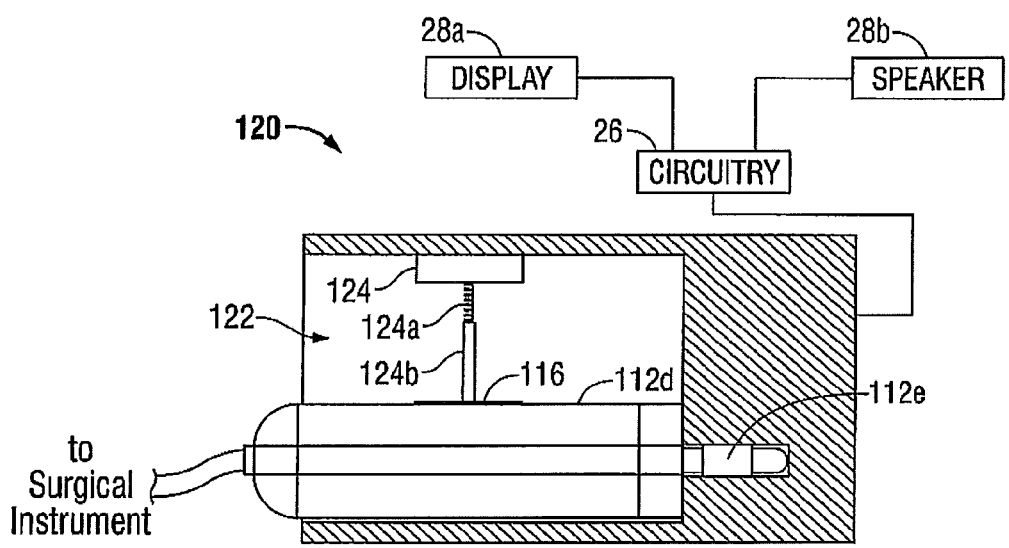
FIG. 5 is a side view of a plug positioned within a receptacle of an energy source, in accordance with another embodiment of the present disclosure.

FIG. 5 illustrates another embodiment that provides generator 20 including a sensor 124 having a biasing member 124a and a sensor tip 124b. Sensor tip 124b may be attached to sensor 124 via biasing member 124a. During use, plug 12d may be inserted within receptacle 122 of generator 20. Plug 112d includes a removable ink 116 that is selectively raised to the top surface of the plug 12d. As the plug 112d is inserted within receptacle 122, the raised configuration of removable ink 116 raises the biasing sensor tip 124b and thereby triggers sensor 124 of generator 20. The triggering of sensor 124 indicates to the generator 20, via suitable circuitry 126, that instrument 112 is properly connected and ready for use. When the single-use instrument has been cleaned and/or sterilized after a surgical operation, removable ink 116 partially or fully dissolves such that removable ink 116 is dissolved or distorted. In this second configuration, removable ink 116 is unable to raise biasing tip 124b and, thus, does not trigger sensor 124. that a valid instrument 112 is plugged into the generator 20

The present disclosure also relates to a method for preventing re-use of a single-use instrument. During an initial use, connector plug 12, 112 of electrosurgical instrument 12, 112 is fitted or inserted within receptacle 22, 122 of generator 20, 120 such that optical sensor 24, 124 reads bar code 18a, 18b and verifies the integrity of the instrument 12, 112. As mentioned above, generator 20, 120 may also read logic information (e.g., the bar code 18a, 18b) that enables the electrosurgical instrument 20, 120 to identify the type of instrument that is plugged in and, via suitable circuitry 26, 126, calibrate the instrument 12, 112 for surgical use. For example, a bipolar endoscopic surgical instrument is coupled to the generator 20, 120 such that plug 12d, 112d is inserted therein. Sensor 24, 124 of receptacle 22, 122 reads bar code 18a, 18b positioned on plug 12d, 112d. After a common set of diagnostics and tests, generator 20, 120 determines the type of instrument 12, 112 plugged into the receptacle 22, 122 and conforms the output energy of the instrument 12, 112 in accordance with the type of instrument is inserted therein to the receptacle 22, 122.

After most surgical procedures, a surgical instrument is usually soiled with blood and other surgical and bodily fluids. Thereafter, with a single-use instrument, it is supposed to be discarded as per governmental guidelines. However, it is known that various re-sellers use enzymatic cleaners to clean and sterilize the instruments for re-use. During the sterilization process the instruments are typically "pre-soaked" before entering the autoclave or the ETO sterilizer. In the so-called "pre-soak" process, the blood stains and residue are removed from the surgical instrument 12, 112 and softened or dissolved, in preparation for the autoclave or ETO sterilizer process, using enzymatic cleaning solutions that are configured to break down proteins associated with blood.

Since blood cleaners (e.g., enzyme-containing cleaners) are able to break down blood protein and other surgical residue, it is envisioned that the blood cleaners will also break down the removable ink 16, 116 since the ink is composed of protein. In this manner, when plug 12d, 112d or instrument 12, 112 is re-inserted into receptacle 22, 122 of generator 20, 120 (or otherwise presented for validation), sensor 24, 124 of generator 20, 120 or the scanning device 23a, 23b is unable to read removable ink 16, 116. That is, the break down or substantial removal of removable ink 16, 116 causes generator 20, 120 to provide an error message since removable ink 16, 116 is unable to be read by the sensor 24, 124.

From the foregoing it is known that certain modifications may be made to the embodiments described herein without departing from the scope of the disclosure. For example, it is contemplated that the label 16a or removable ink 16 may be disposed on the instrument 12 and read by a scanning device, for example, a magnetic scanner, an optical sensor 24 and/or scanner or reader 23a, 23b associated with the electrosurgical energy source. In this manner, prior to use the user validates the integrity of the instrument by scanning the instrument 12 with the scanning device and upon validation the operator may use the instrument as intended for a particular surgical procedure. Once the instrument is cleaned and/or sterilized for subsequent use, the removable ink 16 dissolves or otherwise becomes compromised that makes future validations impossible. In some instances, it may be preferable to stamp the ink 16 onto the instrument 12 during an automated manufacturing process in a particular place or at a particular orientation that will require cleaning or sterilization before reuse, e.g., a working or operating component such as a connector, a housing, a handle, an actuator, a rotation mechanism, an articulation mechanism, a switch, or the like. In this instance, the placement of the bar code 18a, 18b or label 16a will necessitate cleaning by the reseller.

It is also contemplated that a water-soluble ink or other liquid-soluble ink may be employed and a removable liner may be composed of a clear protein-based solution that reacts with the sterilization solution. Once the removable liner is dissolved, the removable ink 16 reacts to dissolve when placed in contact with any solution including water.

It is also contemplated that the removable ink may be configured to react to heat such that the removable ink melts under typical autoclave conditions rendering the ink unreadable by one or more of the above scanning devices.

While several embodiments of the disclosure have been shown in the drawings, it is not intended the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed:

1. A method for preventing re-use of a surgical instrument, comprising:
   electrically coupling a scanning device to an electrosurgical energy source;
   reading a removable ink supported on the surgical instrument with the scanning device, the removable ink including a protein-based composition activateable with a sterilization solution having an enzyme-based composition;
   using the surgical instrument for the surgical instrument's intended purpose; and
   placing the surgical instrument into the sterilization solution to at least partially dissolve the removable ink rendering the removable ink unreadable.

2. The method for preventing re-use of a surgical instrument according to claim 1 further including configuring the removable ink in the form of at least one of a one-dimensional code, a two-dimensional code, and a three-dimensional code.

3. The method for preventing re-use of a surgical instrument according to claim 1 further including applying the removable ink to at least a portion of the surgical instrument.

4. The method for preventing re-use of a surgical instrument according to claim 3 wherein applying the removable ink to at least a portion of the surgical instrument includes applying the removable ink to at least one of a connector, a shaft, a housing, an end effector, a handle, an actuator, a rotation mechanism, an articulation mechanism, and a switch.

5. The method for preventing re-use of a surgical instrument according to claim 1 further including applying the removable ink to a label and securing the label to the surgical instrument.

6. The method for preventing re-use of a surgical instrument according to claim 1 further including:
   disposing a liner atop the removable ink to protect the removable ink during handling; and
   removing the liner prior to using the surgical instrument.

7. The method of preventing re-use of a surgical instrument according to claim 1 further including attempting to validate the surgical instrument for re-use by scanning the removable ink with the scanning device.

\* \* \* \* \*